(12) United States Patent
Balgobin

(10) Patent No.: US 7,691,124 B2
(45) Date of Patent: Apr. 6, 2010

(54) DELIVERY OF THERAPEUTIC DEVICES

(75) Inventor: Keith Balgobin, Pembroke Pines, FL (US)

(73) Assignee: Codman & Shurtleff, Inc., Raynham, MA (US)

( * ) Notice: Subject to any disclaimer, the term of this patent is extended or adjusted under 35 U.S.C. 154(b) by 386 days.

(21) Appl. No.: 11/344,989

(22) Filed: Jan. 31, 2006

(65) Prior Publication Data

US 2007/0179588 A1   Aug. 2, 2007

(51) Int. Cl.
*A61M 29/00* (2006.01)
*A61F 2/06* (2006.01)

(52) U.S. Cl. .................. 606/200; 606/191; 606/195; 606/206; 623/1.11

(58) Field of Classification Search ........... 606/108, 606/191, 206, 198, 200; 604/57, 94.01, 195; 623/1.11
See application file for complete search history.

(56) References Cited

U.S. PATENT DOCUMENTS

| | | | | |
|---|---|---|---|---|
| 5,108,407 A | * | 4/1992 | Geremia et al. | 606/108 |
| 5,224,954 A | | 7/1993 | Watts et al. | |
| 5,250,071 A | | 10/1993 | Palermo | |
| 5,520,697 A | * | 5/1996 | Lindenberg et al. | 606/108 |
| 5,578,074 A | | 11/1996 | Mirigian | |
| 5,746,769 A | * | 5/1998 | Ton et al. | 606/206 |
| 5,814,062 A | * | 9/1998 | Sepetka et al. | 606/198 |
| 5,891,155 A | * | 4/1999 | Irie | 606/108 |
| 5,895,391 A | * | 4/1999 | Farnholtz | 606/108 |
| 5,989,242 A | * | 11/1999 | Saadat et al. | 606/1 |
| 6,723,108 B1 | | 4/2004 | Jones et al. | |
| 6,849,081 B2 | | 2/2005 | Sepetka et al. | |
| 7,367,987 B2 | * | 5/2008 | Balgobin et al. | 606/200 |
| 7,371,251 B2 | * | 5/2008 | Mitelberg et al. | 606/200 |
| 2001/0002438 A1 | | 5/2001 | Sepetka et al. | |
| 2005/0149108 A1 | | 7/2005 | Cox | |
| 2005/0222605 A1 | | 10/2005 | Greenhalgh et al. | |
| 2006/0025802 A1 | * | 2/2006 | Sowers | 606/200 |
| 2006/0025803 A1 | * | 2/2006 | Mitelberg et al. | 606/200 |

OTHER PUBLICATIONS

European Search Report in 07250340.2 dated Apr. 4, 2007.

* cited by examiner

*Primary Examiner*—(Jackie) Tan-Uyen T. Ho
*Assistant Examiner*—Mark Mashack
(74) *Attorney, Agent, or Firm*—Cook Alex Ltd.

(57) ABSTRACT

Therapeutic devices, especially vaso-occlusive devices or embolic coils, are delivered by an apparatus that includes a pullwire having a tine or tines that have an offset orientation that engages a therapeutic device. The pullwire passes through an opening of a headpiece. When the pullwire moves in a relative proximal direction, the tine moves toward a straight-line orientation, and the therapeutic device is liberated from the tine and from the pullwire. At this state, the therapeutic device is ready for deployment at a desired intraluminal location.

16 Claims, 1 Drawing Sheet

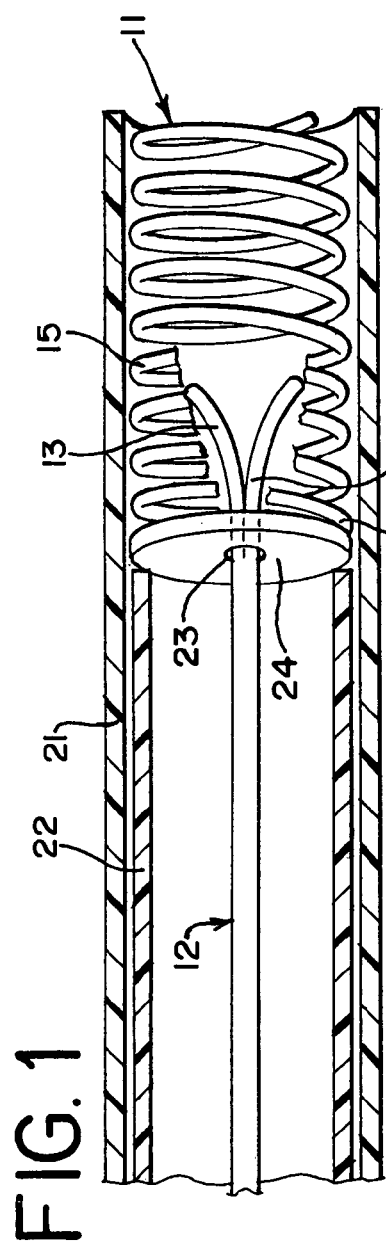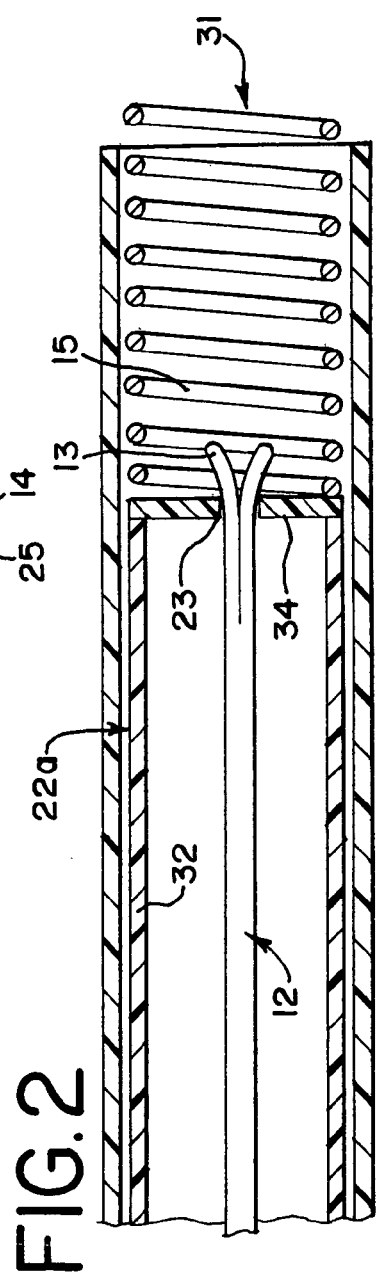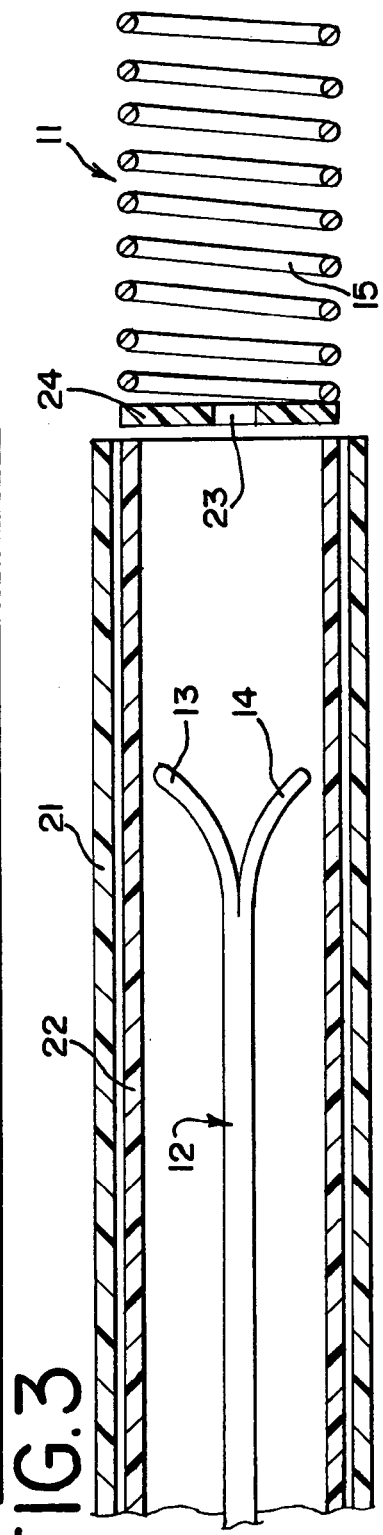

DELIVERY OF THERAPEUTIC DEVICES

FIELD OF THE INVENTION

The invention relates generally to the delivery of therapeutic devices in the vasculature of mammals. The disclosure describes apparatuses and methods for accurately and rapidly delivering a therapeutic device at a desired location.

BACKGROUND OF THE INVENTION

The use of catheters to insert and position therapeutic devices in the vasculature has become a widely-used form of treatment for various conditions. Such devices are particularly useful in treating areas where traditional procedures are difficult such as in narrow cranial blood vessels. For example, vaso-occlusive devices such as embolic coils or wires are inserted at sites of aneurysm to occlude blood flow. The decreased blood flow reduces the pressure on the aneurysm and reduces the risk of a ruptured aneurysm. The coil also promotes thrombus formation. Embolic coils and wires can assume different shapes to better occlude a blood vessel. The coils can be coated with various materials to improve thrombogenicity. U.S. Pat. No. 6,723,108 describes some of the characteristics of different shapes of embolic coils. This patent and all other patents and references identified herein are hereby incorporated herein by reference.

Typically, procedures using a catheter involve inserting the distal end of the catheter into the vasculature of a patient and guiding it to a predetermined delivery site. A therapeutic device, such as an embolic coil, is attached to the distal end of a pusher element such as a wire that can be used to manipulate the therapeutic device. For example, the wire is used to push the coil through the catheter and out of its distal end into the delivery site. The coil is then released from the pusher element. The small sizes of some blood vessels require that a mechanism which releases the coil from the pusher be simple and not required complicated equipment. In addition, the release must accurately and rapidly place the therapeutic device at the determined site. Problems that have been associated with the release of the coil include the force of the coil exiting the delivery catheter causing the coil to overshoot the desired site or dislodge previously deployed coils.

In response to the above mentioned concerns, numerous devices and release mechanisms have been developed in an attempt to provide a delivery system which provides a rapid release or detachment mechanism to release the device at the correct location. One such device is disclosed in Geremia et al. U.S. Pat. No. 5,108,407, which shows a fiber optic cable including a connector device mounted to the end to the optic fiber. An embolic coil is attached to the connector device by a heat releasable adhesive. Laser light is transmitted through the fiber optic cable to increase the temperature of the connector device, which melts the adhesive and releases the embolic coil. One drawback to using this type of system is the potential risk of melted adhesives contaminating the blood stream.

Yet another embolic coil positioning and delivery system is described in Saadat et al. U.S. Pat. No. 5,989,242, which discloses a catheter having a shape memory alloy connector attached to the distal end of the catheter. The connector includes a socket having a pair of spaced-apart fingers which are responsive to a change in temperature. The fingers are bent towards each other and hold a ball which is connected to an end of an embolic coil. The connector absorbs laser light transmitted through an optical cable and transforms the light into heat energy. The heat energy raises the temperature of the connector and opens the fingers, thereby releasing the embolic coil. This type of ball and socket connection is rigid and causes the catheter to be stiff, making it difficult to guide the catheter through the vasculature of the body.

In keeping with the invention, a need is recognized for a rapid, simple therapeutic device delivery apparatus that is elegant in design, relatively simple to manufacture, flexible and easy to guide through the vasculature of the body and which provides excellent control over the device.

SUMMARY OF THE INVENTION

According to one embodiment of the invention, the apparatus consists of a pullwire that has at least one tine present at its distal end. The pullwire is used to manipulate the therapeutic device. The tine is capable of engaging with the therapeutic device such that the pullwire can be used to manipulate the position of the therapeutic device. To engage the therapeutic device, the tine assumes an offset or expanded configuration. In a system concerning the invention, the pullwire and therapeutic device can be enclosed in a guide tube such as a catheter. To release the therapeutic device from its engagement with the pullwire, there is relative movement between the pullwire and a headpiece such that the pullwire is drawn through an opening in the headpiece. The size of the opening forces the tine into a generally straight-line, or collapsed or unexpanded configuration, and the tine is disengaged from the therapeutic device, which is ready for intraluminal deployment.

Vaso-occlusive devices such as embolic coils represent one preferred therapeutic device that can be used with the apparatus.

The tine or tines can vary in both length and in number. The tine can be formed from the same piece of material used to form the pullwire by, for example, splitting the end of the material. Alternatively, the tine can be formed of the same or different materials and attached to the distal end of the pullwire. The tine can be formed from a resilient material. Shape memory metals are a preferred material.

The headpiece provides a draw-down opening for sliding engagement with the pullwire. The headpiece can be attached to either the proximal end of the therapeutic device or to the distal end of the guide tube.

A general aspect of the invention is to provide a delivery apparatus for the delivery of a therapeutic device in a patient and methods for using same.

Another aspect or object of the present invention is to provide an improved system and method for intraluminal delivery of vaso-occlusive devices, especially for intracranial use, said system having minimal moving components.

Other aspects, objects and advantages of the present invention will be understood from the following description according to the preferred embodiments of the present invention, specifically including stated and unstated combinations of the various features which are described herein, relevant information concerning which is shown in the accompanying drawing.

BRIEF DESCRIPTION OF THE DRAWINGS

In describing the preferred embodiments of the present invention, reference will be made to the accompanying drawings, wherein:

FIG. 1 is a perspective view of the therapeutic device delivery apparatus or system in accordance with a preferred embodiment of the present invention. In this view two tines are shown engaged with an embolic coil.

FIG. 2 is a sectional view of another embodiment, shown at a stage where two tines and pullwire are being pulled to disengage from the therapeutic device; and FIG. 3 is a sectional view of the system illustrated in FIG. 1, showing the complete disengagement of two tines and pullwire from the therapeutic device.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

As shown in FIGS. 1-3, the present disclosure provides for delivery and release of therapeutic devices, such as the illustrated embolic coil, which is generally designated at 11. This is embodied in devices, systems and methods that are illustrated herein as preferred embodiments.

According to one embodiment, the invention consists of a pullwire, generally designated at 12, that has one or more tines 13, 14 at the distal end of the pullwire 12. Each tine can assume a configuration where it is at an offset, non-straight-line or expanded state. As shown in FIG. 1, one or more tine will engage with the therapeutic device 11 in this offset configuration so as to grasp the therapeutic device in order to maneuver the device to a desired location within the vasculature. For example, as shown in FIG. 1, each tine may engage an embolic coil by intertwining with or interleaving between and pushing against one or more turns 15 of the embolic coil. When two tines 13, 14 are provided, they together may assume a V-shape when engaged with the therapeutic device. Consequently, the engaged therapeutic device 11 such as the illustrated embolic coil can be manipulated by moving the pullwire 12.

As shown in FIG. 1, the pullwire 12 and therapeutic device 11 may be enclosed in a guide tube 21 such as a catheter to guide and position the therapeutic device and pullwire. A pusher 22 is provided which is slidably positioned within the guide tube 21. At the desired location in the body of the patient, the guide tube 21 and the pullwire 12 (with engaged therapeutic device) move relative to each other. Either the guide tube is moved retrograde or the therapeutic device 11 is pushed out of the tube such that the therapeutic device is placed at the desired location within the patient, such as in or at an aneurysm.

To release the therapeutic device from the pullwire, relative movement between the pullwire 12 and the pusher 22 is effected. According to one approach, a proximal portion (not shown) of the pullwire that is external to the patient is pulled proximally, typically beyond the proximal end of the guide tube 21, which also is external of the patient. This continues until the pullwire is fully disengaged from the therapeutic device. According to another approach, the pullwire remains relatively stationary and the pusher 22 is moved distally, thereby moving the therapeutic device distally to slide it off of the pullwire.

By either approach, each tine disengages from the therapeutic device and slides through and out of an opening 23 in a headpiece 24 to a position similar to that shown in FIG. 2. As relative pullwire movement continues in this proximal direction, each tine 13 is forced into a generally straight-line orientation at which the straightening effect being illustrated in FIG. 2 continues until virtually all of the tine is straightened so as to have a longitudinal axis along or parallel to the axis of the pullwire 12, which can be referred to as an unexpanded or collapsed configuration, when passing through the opening.

In the embodiment shown in FIG. 1, the headpiece 24 is a component of the embolic device 11 and is attached to the coil at the proximal end 25 of the coil 15. In the embodiment shown in FIG. 2, a headpiece 34 is secured to a body 32 of the pusher of that embodiment. The illustrated embolic device 31 has no headpiece type of component, and can be essentially a coil. Another proximal end component (not shown) could be part of embolic device 31, which component would be deployed together with the coil of such an embolic device. In either approach, each tine 13 slides through opening 23 in a proximal direction until it disengages the headpiece 24 or 34.

In FIG. 3, each tine 13 is shown completely disengaged from the embolic device 11. The pullwire 12 and guide tube 21 are withdrawn, leaving the coil in the desired location. As shown in FIG. 3, when disengaged from the therapeutic device and the headpiece, the tines may reassume an expanded configuration offset from the straight-line configuration that exists when the tine passes through the opening 23.

With further reference to the alternative embodiment illustrated in FIG. 2, the headpiece 34 with opening 23 is attached to the distal end of the pusher 22a by suitable means known in the art. Alternatively, the headpiece 34 and pusher body 32 are integrally formed. Each tine engages with the therapeutic device as shown in the FIG. 1 embodiment. Also, as in the FIG. 1 embodiment, each tine is disengaged from the therapeutic device by relative movement between the pullwire 12 and the headpiece, such as by pulling the pullwire in a proximal direction through the pusher and/or guide tube. The pullwire and pusher body 32 with headpiece 34 are withdrawn from the body of the patient, leaving the embolic device 31 at the desired location.

In one embodiment, each tine is formed from the same piece of material used to manufacture the pullwire by, for example, splitting the distal end of the rod or the like from which the pullwire is made. This type of unitary construction is preferred due to its relative simplicity. It also is preferred because the unitary approach avoids a possibility of failure of an attachment of a tine to a pullwire should an alternative embodiment be followed, such as one where the tine is manufactured from a separate piece of material and securely attached to the pullwire by means known in the art.

As noted previously, one or more tine 13, 14 can be provided at the distal end portion of the pullwire 12. In the preferred embodiment that is illustrated, two tines are provided that are of approximately the same length and at approximately the same degree of offset from the longitudinal axis of the pullwire when in their offset configuration such as shown in FIG. 1. According to different embodiments, it is possible that only a single tine be provided so long as it securely engages and holds the embolic device. Also, multiple tines may have different sizes or lengths, and they may be offset from the longitudinal axis of the pullwire to different extents. Furthermore, there may be greater than two tines of the same size and orientation or having variations as noted.

The material of each tine needs to have adequate shape properties so the tine will be in the offset, non-straight-line configuration when in use and will remain in that condition to provide adequate holding power when engaging the therapeutic device. The tine must also be flexible enough to readily move to the straight-line orientation in response to transverse forces applied to the tine as it moves through the opening 24. While it is not essential that the tine also be resilient so as to "spring back" to the offset orientation (as illustrated in FIG. 3), this can be a property of the tine. When this latter feature is desired, each tine may be formed from a resilient material or a material having shape memory properties, typically tied to variations in temperature.

Examples of a resilient material include a spring stainless steel or other resilient material suitable for use within the body. Each tine can be manufactured from a material that has shape memory, typically metals or metal alloys or polymers with the desired properties. A nitinol alloy has excellent shape memory attributes and is a preferred metal or alloy.

When an alloy such as a nitinol is at a low temperature, which in this instance would be lower than human body temperature, the pullwire is made such that each tine is at the generally straight-line or unexpanded configuration. At a higher temperature approximating body temperature, each tine is at the offset orientation. With this configuration, the pullwire typically is assembled through the opening in the headpiece when at room temperature or below, which facilitates manufacture of the apparatus by allowing the tines to be easily fed through the opening. When the tines are exposed to a temperature greater than the transition temperature, each tine assumes the expanded state and engages with the coil. This expanded state is maintained when at body temperature when the device is placed in the patient. A preferred range for a transition temperature between the martensite state and the austenite state for a shape memory material such as a nitinol is 10-35° C.

In the event the pullwire and the tine are not formed integrally, they can be formed from different materials. In that instance, the pullwire length that is proximal of the tine or tines need not have the same properties as described herein for the tine or tines. It is preferred that all or part of the pullwire, tine or tines will have radio-opaque properties.

It will be understood that the embodiments of the present invention which have been described are illustrative of some of the applications of the principles of the present invention. Numerous modifications may be made by those skilled in the art without departing from the true spirit and scope of the invention. Various features which are described herein can be used in any combination and are not limited to procure combinations that are specifically outlined herein.

The invention claimed is:

1. A system for intraluminal delivery of a therapeutic device, comprising:
   an elongated guide tube for intraluminal deployment;
   a pusher sized and shaped to be slidably positioned within said guide tube, said pusher having a longitudinal axis, an interior lumen wall and a distal end portion;
   a therapeutic device with a proximal end portion and a distal end portion, the proximal end portion of the therapeutic device and the distal end portion of the pusher are adapted for engagement at an abutment location therebetween;
   a headpiece disk at said abutment location, said headpiece disk including a draw-down opening, said draw-down opening having a longitudinal axis being coaxial with said longitudinal axis of the pusher, and the draw-down opening having an outer perimeter that is radially inwardly spaced away from the lumen wall of said pusher;
   a pullwire having a longitudinal axis generally coaxial with said longitudinal axis of said draw-down opening and positioned through said draw-down opening of the headpiece disk, said pullwire having a proximal end portion and a distal end portion, said pullwire further including at least one tine present at said distal end portion of the pullwire, said tine having a generally straight-line orientation at which the tine engages the outer perimeter of the draw-down opening and an offset orientation at which the tine engages said therapeutic device; and
   said pullwire and said draw-down opening are sized and shaped relative to each other such that said tine moves from said offset orientation toward said generally straight-line orientation when said pullwire moves through said draw-down opening of the headpiece disk in a proximal direction and said tine slidably engages the outer perimeter of the draw-down opening thereby disengaging said tine from said therapeutic device.

2. The system of claim 1, wherein said headpiece disk is a component of the therapeutic device and is positioned at the proximal end portion of the therapeutic device.

3. The system of claim 1, wherein said headpiece disk is a component of the pusher and is located at the distal end portion of the pusher.

4. The system of claim 1, wherein said therapeutic device is an embolic coil.

5. The system of claim 1, wherein said tine of the pullwire is formed from a shape memory alloy.

6. The system of claim 5, wherein said tine of the pullwire is formed from a nickel titanium alloy.

7. The system of claim 1, wherein said tine is integrally formed with the rest of the pullwire.

8. The system of claim 1, including more than one said tine, each being of substantially the same length.

9. The system of claim 8, wherein said tines have substantially the same offset orientation.

10. The system of claim 1, wherein said tine is resilient such that same returns to said offset orientation after being at said generally straight-line orientation.

11. An apparatus for intraluminal delivery of a therapeutic device, comprising:
    a pusher sized and shaped for intraluminal delivery, said pusher having a longitudinal axis, an interior lumen wall and a distal end portion;
    a therapeutic device with a proximal end portion and a distal end portion, the proximal end portion of the therapeutic device and the distal end portion of the pusher are adapted for engagement at an abutment location therebetween;
    a headpiece disk at said abutment location, said headpiece disk including a draw-down opening, said draw-down opening having a longitudinal axis being generally coaxial with said longitudinal axis of the pusher, and the draw-down opening having an outer perimeter that is radially inwardly spaced away from the lumen wall of said pusher;
    a pullwire having a longitudinal axis generally coaxial with said longitudinal axis of said draw-down opening and positioned through said draw-down opening of the headpiece disk, said pullwire having a proximal end portion and a distal end portion, said pullwire further including at least one tine present at said distal end portion of the pullwire, said tine having a generally straight-line orientation at which the tine engages the outer perimeter of the draw-down opening and an offset orientation at which the tine engages said therapeutic device; and
    said pullwire and said draw-down opening are sized and shaped relative to each other such that said tine moves from said offset orientation toward said generally straight-line orientation when said pullwire moves through said draw-down opening of the headpiece disk in a proximal direction and said tine slidably engages the outer perimeter of the draw-down opening thereby disengaging said tine from said therapeutic device.

12. The apparatus of claim 11, wherein said headpiece disk is a component of the therapeutic device and is positioned at the proximal end portion of the therapeutic device.

13. The apparatus of claim 11, wherein said headpiece disk is a component of the pusher and is located at the distal end portion of the pusher.

14. The apparatus of claim 11, wherein said therapeutic device is an embolic coil.

15. The apparatus of claim 11, wherein said tine of the pullwire is formed from a shape memory alloy.

16. The system of claim 1, wherein said therapeutic device is vaso-occlusive.

* * * * *